US012810245B2

(12) United States Patent
Darmour et al.

(10) Patent No.: US 12,810,245 B2
(45) Date of Patent: Nov. 24, 2026

(54) GENERATIVE MODEL FOR CREATING AND PRESENTING MEDICAL ORDERS

(71) Applicant: Oracle International Corporation, Redwood Shores, CA (US)

(72) Inventors: Jennifer Darmour, Seattle, WA (US); Orry Soegiono, Bellevue, WA (US); Micah Lawler Sonderman, San Antonio, TX (US)

(73) Assignee: Oracle International Corporation, Redwood Shores, CA (US)

( * ) Notice: Subject to any disclaimer, the term of this patent is extended or adjusted under 35 U.S.C. 154(b) by 0 days.

(21) Appl. No.: 18/929,450

(22) Filed: Oct. 28, 2024

(65) Prior Publication Data

US 2026/0073352 A1 Mar. 12, 2026

Related U.S. Application Data

(60) Provisional application No. 63/691,577, filed on Sep. 6, 2024.

(51) Int. Cl.

| | |
|---|---|
| ***G06Q 10/087*** | (2023.01) |
| ***G16H 10/60*** | (2018.01) |
| ***H04L 51/02*** | (2022.01) |

(52) U.S. Cl.

CPC .......... *G06Q 10/087* (2013.01); *G16H 10/60* (2018.01); *H04L 51/02* (2013.01)

(58) Field of Classification Search

CPC ....... G06Q 10/087; G16H 10/60; H04L 51/02
See application file for complete search history.

(56) References Cited

U.S. PATENT DOCUMENTS

2024/0428052 A1* 12/2024 Hwang ................. G06N 3/045

OTHER PUBLICATIONS

S.Suma, Apr. 2018, Medicine Prescription System by using Machine Learning, GRD Journals—Global Research and Development Journal for Engineering; vol. 3 (Year: 2018).*

* cited by examiner

*Primary Examiner* — Ariel J Yu
*Assistant Examiner* — Denisse Y Ortiz Roman
(74) *Attorney, Agent, or Firm* — Invoke

(57) ABSTRACT

Techniques for using machine learning models to create and present medical orders for patients are disclosed. These techniques facilitate the identification, selection, and fulfillment of an order, e.g., prescription or treatment, in response to updates to patient data for the patient, e.g., reporting of test results, receipt of messages or referrals, and addition of discussions. The system monitors, in real time, updates to the patient data. The patient data may be part of an EHR. When the system determines that content of an update satisfies a trigger for generating an order, the system applies a machine learning model to the patient data to determine an order corresponding to the patient data. The machine learning model generates the order for the patient and presents the order to medical professionals for review.

23 Claims, 8 Drawing Sheets

GENERATIVE MODEL FOR CREATING AND PRESENTING MEDICAL ORDERS

BENEFIT CLAIMS; RELATED APPLICATIONS; INCORPORATION BY REFERENCE

This application claims the benefit of U.S. Provisional Patent Application No. 63/691,577, filed Sep. 6, 2024, which is hereby incorporated by reference.

TECHNICAL FIELD

The present disclosure relates to computerized patient order entry systems. In particular, the present disclosure relates to the use of generative models to assist in creating and presenting medical orders for patients.

BACKGROUND

Computerized patient order entry refers to the process of healthcare providers entering and managing medical orders electronically instead of using paper-based methods. Patient order entry technology is often integrated with electronic health records (EHR) systems in an effort to reduce medical errors, improve patient safety, and streamline healthcare delivery.

Medical professionals or clinicians, e.g., physicians, nurses, or other authorized staff, enter orders into the system for various patient needs, such as laboratory tests, radiology exams, medications, and procedures. The patient order system may include standardized templates and order sets for common diagnoses or treatment plans to ensure consistency and accuracy. Orders are electronically transmitted to the appropriate entity, e.g., pharmacy, laboratory, radiology, for fulfillment.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The embodiments are illustrated by way of example and not by way of limitation in the figures of the accompanying drawings. It should be noted that references to "an" or "one" embodiment in this disclosure are not necessarily to the same embodiment, and they mean at least one. In the drawings.

DETAILED DESCRIPTION

Figure 1:
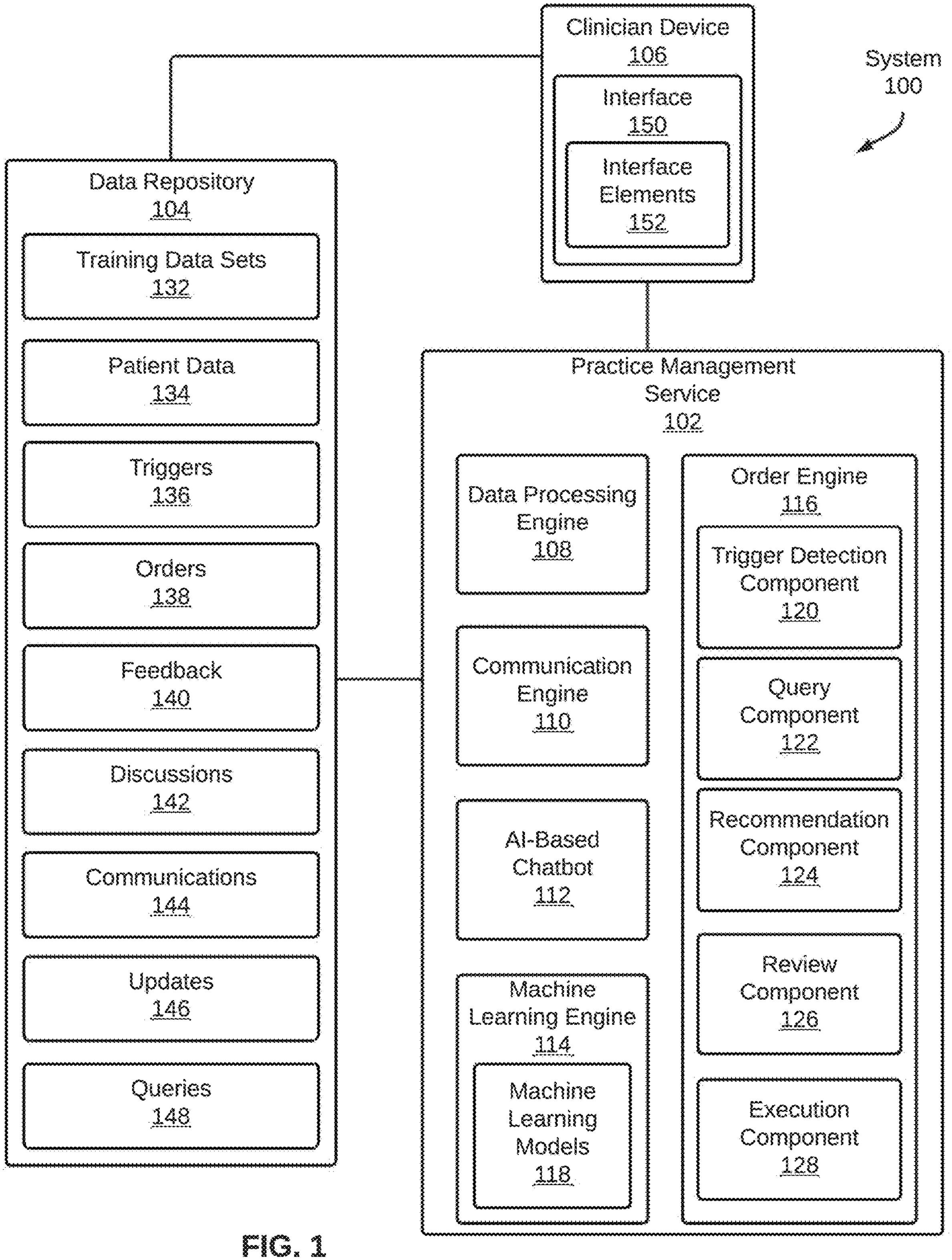
FIG. 1 illustrates a system in accordance with one or more embodiments.

In the following description, for the purposes of explanation, numerous specific details are set forth to provide a thorough understanding. One or more embodiments may be practiced without these specific details. Features described in one embodiment may be combined with features described in a different embodiment. In some examples, well-known structures and devices are described with reference to a block diagram form to avoid unnecessarily obscuring the present disclosure.

1. GENERAL OVERVIEW
2. PATIENT MANAGEMENT SYSTEM ARCHITECTURE
3. DETERMINING AN ORDER FOR A PATIENT USING MACHINE LEARNING
4. DETERMINING A PATIENT FOR AN ORDER
5. DETERMINING MISSING CONTENT FOR ORDER COMPLETION
6. DASHBOARD FOR A PATIENT MANAGEMENT SYSTEM
7. CHAT CONVERSATION IN A PATIENT MANAGEMENT SYSTEM
8. PRACTICAL APPLICATIONS, ADVANTAGES & IMPROVEMENTS
9. HARDWARE OVERVIEW
10. MISCELLANEOUS; EXTENSIONS

1. GENERAL OVERVIEW

One or more embodiments apply machine learning techniques for creating and presenting medical orders for patients. The techniques facilitate the identification, selection, and fulfillment of an order, e.g., prescription or treatment, in response to updates to patient data for the patient, e.g., test results, messages, or referrals. The system monitors, in real time, updates to patient data stored in an electronic health record. When the system determines that content of an update satisfies a trigger for generating an order, the system applies a machine learning model to the patient data to determine an order corresponding to the patient data. The machine learning model generates the order for the patient and presents the order to medical professionals for review.

One or more embodiments identify and present candidate patients for an order as the clinician prepares the order. The system receives user input for an order. Concurrently with receiving or subsequent to receiving the user input, the system generates and executes a query to determine a candidate set of one or more patients for the order. The candidate set of one or more patients for the order is presented for application of the order. The candidate set of patients may include patients that have recently visited with the clinician or patients that have visited with the clinician within a particular window of time. As additional information is received for an order, the system may modify the candidate set of one or more patients based on the additional information.

One or more embodiments review and complete medical orders for patients. The system reviews an order entered by a clinician into a graphical user interface (GUI). The system determines if the order satisfies the requirements for completing the order, e.g., dosage, frequency, duration, etc. When the system determines that the order is incomplete, i.e., elements for completing the order are missing, the system identifies the missing elements and displays the missing elements on the GUI for clinician review and rectification. Upon receipt of the missing elements, the system determines that the order is complete and presents an interface element to the clinician for executing the order.

One or more embodiments described in this Specification and/or recited in the claims may not be included in this General Overview section.

2. PATIENT MANAGEMENT SYSTEM ARCHITECTURE

FIG. 1 illustrates a system 100 in accordance with one or more embodiments. As illustrated in FIG. 1, system 100 includes a practice management service 102, a data repository 104, and a clinician device 106. In one or more embodiments, the system 100 may include more or fewer components than the components illustrated in FIG. 1. The components illustrated in FIG. 1 may be local to or remote from one another. The components illustrated in FIG. 1 may be implemented in software and/or hardware. The component may be distributed over multiple applications and/or machines. Multiple components may be combined into one application and/or machine. Operations described with respect to one component may instead be performed by another component.

In one or more embodiments, practice management service 102 refers to hardware and/or software configured to perform operations described herein for using machine learning to create and present medical orders. Examples of operations for using machine learning to create and present medical orders are described below with reference to FIGS. 2-4.

In an embodiment, practice management service 102 is implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a hardware router, a hardware switch, a hardware firewall, a hardware network address translator (NAT), a hardware load balancer, a mainframe, a television, a content receiver, a set-top box, a printer, a mobile handset, a smartphone, a personal digital assistant (PDA), a wireless receiver and/or transmitter, a base station, a communication management device, a router, a switch, a controller, an access point, and/or a client device.

In one or more embodiments, the practice management service 102 assists healthcare providers in managing patient information, orders, appointments, and various other tasks necessary for the efficient functioning of the practice. The practice management service 102 includes a data processing engine 108, a communication engine 110, an AI-based chatbot 112, a machine learning engine 114, and an order engine 116.

In one or more embodiments, data processing engine 108 refers to hardware and/or software configured to perform operations described herein for processing and managing patient data within the system 100. The data processing engine 108 ensures that patient data is accurately captured, stored, and analyzed to support various functions such as patient care, administrative tasks, and decision-making processes.

In one or more embodiments, the data processing engine 108 performs operations including data ingestion and integration, data transformation and normalization, data storage and management, data analytics and reporting, and real-time data processing. Data ingestion and integration includes collecting data from various sources, such as electronic health records (EHR), lab systems, imaging systems, and patient registration forms and integrating data from disparate systems to create a unified patient record. Data transformation and normalization includes transforming raw data into a standardized format that can be easily used and understood across the system and normalizing data to ensure consistency and accuracy, such as converting various date formats into a single standard. Data storage and management includes efficiently storing large volumes of patient data in databases, ensuring quick retrieval and secure access, and managing data lifecycle, including archival and deletion of outdated records in compliance with regulatory requirements. Data analytics and reporting include (1) providing tools for analyzing patient data to generate insights and support clinical decision making and (2) generating reports and dashboards for monitoring practice performance, patient outcomes, and operational efficiency. Real-time data processing includes enabling real-time processing of data for immediate use, such as updating patient records during a clinical encounter, alerting providers to critical lab results, and supporting real-time monitoring and alerts for patient conditions.

In one or more embodiments, communication engine 110 is software and/or hardware configured to perform operations described herein for facilitating communication between clinicians, patients, and administrative staff. The communication engine 110 ensures that information is shared promptly and securely, enhancing patient care, improving operational efficiency, and promoting patient engagement.

In one or more embodiments, the communication engine 110 provides secure messaging, patient portals, automated notification and reminders, and integration with EHR. Secure messaging includes medical professional-to-medical professional communication, medical professional-to-patient communication, and internal messaging. Patient portals provide patient access to health information, appointment scheduling, and direct messaging. Automated notifications and reminders include appointment reminders, medication reminders, and follow-up reminders. Integration with EHR includes data synchronization and audit trails.

In one or more embodiments, AI-based chatbot 112 is software and/or hardware configured to perform operations described herein for providing decision support, streamlining administrative tasks, and improving patient care. The AI-based chatbot 112 leverages artificial intelligence, machine learning, and natural language processing (NLP) to assists clinicians in various aspects of the healthcare practice.

In one or more embodiments, the AI-based chatbot 112 provides clinical decision support, EHR integration, appointment management, and task management. Clinical decision support includes symptom assessment, access to clinical guidelines, treatment protocols, best practices, and drug information, e.g., drug interactions, dosages, and side effects. EHR integration includes patient record access and documentation assistance. Task management includes maintaining to-do lists and providing notifications, e.g., alerts for urgent tasks, lab results, or messages from patients.

In one or more embodiments, one or more components of the practice management service 102 use a machine learning engine 114. Machine learning includes various techniques in the field of AI that deal with computer-implemented, user-independent processes for solving problems that have variable inputs.

In embodiment, the machine learning engine 114 trains a machine learning model 118 to perform one or more operations. Training a machine learning model 118 uses training data to generate a function that, given one or more inputs to the machine learning model 118, computes a corresponding output. The output may correspond to a prediction based on prior machine learning. In some embodiments, the output includes a label, classification, and/or categorization assigned to the provided input(s). The machine learning model 118 corresponds to a learned model for performing the desired operation(s) (e.g., labeling, classifying, and/or categorizing inputs). The practice management service 102 may use multiple machine learning engines 114 and/or multiple machine learning models 118 for different purposes.

In some embodiments, the machine learning engine 114 may use supervised learning, semi-supervised learning, unsupervised learning, reinforcement learning, and/or another training method or combination thereof. In supervised learning, labeled training data includes input/output pairs in which each input is labeled with a desired output (e.g., a label, classification, and/or categorization), also referred to as a supervisory signal. In semi-supervised learning, some inputs are associated with supervisory signals, whereas other inputs are not associated with supervisory signals. In unsupervised learning, the training data does not include supervisory signals. Reinforcement learning uses a feedback system in which the machine learning engine 114 receives positive and/or negative reinforcement in the process of attempting to solve a particular problem (e.g., to optimize performance in a particular scenario according to one or more predefined performance criteria). In some embodiments, the machine learning engine 114 initially uses supervised learning to train the machine learning model 118 and then uses unsupervised learning to update the machine learning model 118 on an ongoing basis.

In some embodiments, a machine learning engine 114 may use many different techniques to label, classify, and/or categorize inputs. A machine learning engine 114 may transform inputs into feature vectors that describe one or more properties ("features") of the inputs. The machine learning engine 114 may label, classify, and/or categorize the inputs based on the feature vectors. Additionally, or alternatively, a machine learning engine 114 may use clustering (also referred to as cluster analysis) to identify commonalities in the inputs. The machine learning engine 114 may group (i.e., cluster) the inputs based on those commonalities. The machine learning engine 114 may use hierarchical clustering, k-means clustering, and/or another clustering method or combination thereof. In some embodiments, a machine learning engine 114 includes an artificial neural network. An artificial neural network includes multiple nodes (also referred to as artificial neurons) and edges between nodes. Edges may be associated with corresponding weights that represent the strengths of connections between nodes, that the machine learning engine 114 adjusts as machine learning proceeds. Additionally, or alternatively, a machine learning engine 114 may include a support vector machine. A support vector machine represents inputs as vectors. The machine learning engine 114 may label, classify, and/or categorizes inputs based on the vectors. Additionally, or alternatively, the machine learning engine 114 may use a naive Bayes classifier to label, classify, and/or categorize inputs. Additionally, or alternatively, given a particular input, a machine learning model may apply a decision tree to predict an output for the given input. Additionally, or alternatively, a machine learning engine 114 may apply fuzzy logic in situations where labeling, classifying, and/or categorizing an input among a fixed set of mutually exclusive options is impossible or impractical. The aforementioned machine learning model 118 and techniques are discussed for exemplary purposes and should not be construed as limiting some embodiments.

In some embodiments, as a machine learning engine 114 applies different inputs to a machine learning model 118, the corresponding outputs are not always accurate. As an example, the machine learning engine 114 may use supervised learning to train a machine learning model 118. After training the machine learning model 118, if a subsequent input is identical to an input that was included in labeled training data and the output is identical to the supervisory signal in the training data, then output is certain to be accurate. If an input is different from inputs that were included in labeled training data, then the machine learning engine 114 may generate a corresponding output that is inaccurate or of uncertain accuracy. In addition to producing a particular output for a given input, the machine learning engine 114 may be configured to produce an indicator representing a confidence (or lack thereof) in the accuracy of the output. A confidence indicator may include a numeric score, a Boolean value, and/or any other kind of indicator that corresponds to a confidence (or lack thereof) in the accuracy of the output.

In one or more embodiments, order engine 116 is software and/or hardware configured to perform operations described herein for creating, managing, and executing medical orders. The order engine 116 automates and optimizes the ordering process, ensuring accuracy, compliance, and timely execution.

In some embodiments, order engine 116 includes a trigger detection component 120. A trigger detection component 120 is software and/or hardware configured to perform operations described herein for identifying specific events or conditions that may necessitate creation or modification of medical orders.

In some embodiments, order engine 116 includes a query component 122. A query component 122 is software and/or hardware configured to dynamically generate and execute database queries based on user inputs in real time. The query component 122 may use machine learning for generating and/or executing the queries.

In some embodiments, order engine 116 includes a recommendation component 124. A recommendation component 124 is software and/or hardware configured to provide clinicians with actionable suggestions based on patient data. The recommendation component 124 may use machine learning to provide suggestions for medication orders, diagnostic tests, referrals, and consultations.

In some embodiments, order engine 116 includes a review component 126. A review component 126 is software and/or hardware configured to perform operations described herein for evaluating, validating, and finalizing medical orders. The review component 126 uses machine learning to ensure that orders are accurate and complete.

In some embodiments, order engine 116 includes an execution component 128. An execution component 128 is software and/or hardware configured to perform operations described herein for carrying out and managing medical orders once the orders are reviewed and approved. The execution component 128 uses machine learning to ensure that orders are executed accurately and efficiently and that associated tasks and follow-ups are managed.

In one or more embodiments, a data repository 104 is any type of storage unit and/or device (e.g., a file system, database, collection of tables, or any other storage mechanism) for storing data. Furthermore, a data repository 104 may include multiple different storage units and/or devices. The multiple different storage units and/or devices may or may not be of the same type or located at the same physical site. Furthermore, a data repository 104 may be implemented or executed on the same computing system as practice management service 102 and clinician device 106. Additionally, or alternatively, a data repository 104 may be implemented or executed on a computing system separate from practice management service 102 and clinician device 106. The data repository 104 may be communicatively coupled to practice management service 102 and clinician device 106 via a direct connection or via a network.

Information describing the practice management service 102 may be implemented across any of components within the system 100. However, this information is illustrated within the data repository 104 for purposes of clarity and explanation.

In one or more embodiments, training data sets 132 are collections of data used to train machine learning models 118. Training data sets 132 include features, i.e., input variables, and corresponding labels, i.e., target variables. Training data sets 132 may be organized as structured data, e.g., tables, unstructured data, e.g., images, and/or semi-structured data, e.g., JSON or XML documents. An example training data set includes sets of patient data corresponding to patients, i.e., input variables, and one or more orders for a prescription or treatment that are responsive to the patient data, i.e., target variable.

In one or more embodiments, patient data 134 refers to any information about a patient that is collected during the course of the healthcare of the patient. Patient data 134 may be received from a variety of sources and may include a wide range of information types. Patient data 134 may include demographic data, e.g., age, gender, ethnicity, address, and contact details; medical history, e.g., records of past medical conditions, surgeries, treatments, and hospitalizations; clinical data, e.g., information obtained from medical examinations, including physical exams, vital signs, and symptoms; diagnostic data, e.g., results from laboratory tests (blood tests, urine tests, etc.), imaging studies (X-rays, MRIs, CT scans), and pathology reports; and, medication data, e.g., details about current and past medications, including dosages, frequency, and any adverse reactions or allergies. Patient data 134 may also include treatment data, e.g., information about ongoing treatments, including surgeries, therapies, and other interventions; progress notes, e.g., notes made by healthcare providers documenting patient encounters, observations, and treatment plans; administrative data, e.g., information related to healthcare administration, such as insurance details, billing records, and appointment schedules; behavioral data, e.g., information about lifestyle factors, such as smoking status, alcohol consumption, diet, and exercise habits; patient-generated data, e.g., data collected directly from patients, such as through surveys, wearable devices, or home monitoring equipment.

In one or more embodiments, patient data 132 may be received from electronic health records (EHRs), personal health records (PHRs), laboratory information systems (LIS), radiology information systems (RIS), picture archiving and communication systems (PACS), pharmacy information systems (PIS), wearable devices and remote monitoring systems, patient portals, insurance claim data, and Health Information Exchanges (HIEs). EHRs are digital versions of patients' paper charts that provide real-time, patient-centered records accessible to authorized healthcare providers. PHRs are health records maintained by patients themselves, often through digital platforms or mobile apps. LIS are systems that manage lab test orders and results, integrating with EHRs and other hospital information systems. RIS and PACS are systems that manage radiological records and imaging data. PIS are systems that manage medication orders, dispensing, and inventory in healthcare settings. Wearable devices and remote monitoring systems include various devices, such as fitness trackers, heart rate monitors, and glucose monitors, that collect health data outside traditional healthcare settings. Patient portals are online platforms that provide patients with access to their health information, appointment scheduling, and communication with healthcare providers. Insurance claims data is data generated from insurance claims that provide information on diagnoses, treatments, and healthcare utilization. HIEs are networks that enable the sharing of health information across different healthcare organizations and systems.

In one or more embodiments, triggers 136 are a codified set of rules and/or a set of automatically learned patterns that capture one or more conditions for prompting creation or modification of medical orders. Triggers 136 may relate to updates of clinical data in patient data 134. For example, triggers 136 may include updates to the patient data 130 of abnormal lab results, abnormal vital signs, diagnostic imaging results, and updated symptom reports. For example, updates including lab values outside normal ranges, e.g., high blood glucose levels, may trigger an order for insulin. Abnormal vital signs, e.g., high blood pressure or low oxygen saturation, may trigger an order for medication or supplemental oxygen. In another example, receipt of an abnormal lab result, e.g., blood test showing high potassium levels (hyperkalemia), triggers the system to generate an order for a repeat test and possible potassium-lowering treatment, e.g., calcium gluconate, insulin, and glucose. Triggers 136 may result from the system receiving the update, i.e., results from a laboratory, or a clinician viewing the update, i.e., on a GUI.

In one or more embodiments, triggers 136 are based, at least in part, on updates to treatment and protocol guidelines. Treatment protocols and guidelines include standardized care protocols and preventative care guidelines. A standardized care protocol may include clinical pathways for specific conditions, e.g., initiating anticoagulation therapy for patients diagnosed with atrial fibrillation. An update to patient data that includes a diagnosis of atrial fibrillation may trigger generation of an order for anticoagulation therapy. Preventive care guidelines may include routine orders based on age and health status, e.g., vaccination reminders for flu shots. Updates to the patient data based on lapsed time or age of the patient may include a status update for test results from "up-to-date" to "outdated". In an example, an update to the patient data indicating the patient is diabetic may trigger the system to automatically generate an order for the HbA1c test.

In one or more embodiments, triggers 136 are based, at least in part, on medication management or disease management. Medication management may include medication reconciliation or drug interaction notification. Detecting discrepancies or needs for refills, e.g., patient reaching the end of a prescription course, may trigger a refill order. Identifying potential drug-interactions may prompt a review and potential alternative order. Disease management includes chronic disease monitoring. Markers indicating disease progression, e.g., increasing PSA levels in prostate cancer, may prompt an order of further diagnostic tests.

In one or embodiments, triggers 136 are based, at least in part, on procedural and post-operative care or system alerts and reminders. Procedural and post-operative care may include post-operative monitoring and procedure follow-ups. Standard post-surgical orders (e.g., pain management, wound care) may be triggered by an update to the patient data following a procedure. Orders for follow-up on tests may be triggered based on the type of procedure performed, e.g., follow-up colonoscopy based on previous findings. System alerts and reminders include scheduled maintenance and missed appointments. Routine health maintenance checks (e.g., annual physical exams, regular mammograms) may be triggered after the passage of time. Detection of a missed appointment may trigger an order for rescheduling.

In one or more embodiments, triggers 136 are based, at least in part, on patient data integration or administration. Patient data integration includes responses to updates provided by wearable devices and remote monitoring systems. For example, updates to patient data provided by wearable devices, e.g., continuous glucose monitors showing hyperglycemia, may trigger an order for medication adjustment. Administrative triggers include insurance requirements and discharge planning. Compliance with insurance protocols, e.g., pre-authorization for certain tests or treatments, may trigger an order.

In one or more embodiments, orders 138 are instructions given by a healthcare provider that specify the medications, therapies, or other interventions for a patient to receive.

Medication orders include prescription medications, over-the-counter medications (OTC), PRN orders, and standing orders. Prescription medication orders are for drugs that require a prescription, including specifics like dosage, route of administration, frequency, and duration (e.g., "Amoxicillin 500 mg, take one tablet orally three times a day for 10 days"). OTC medications orders are for non-prescription drugs that are recommended by the healthcare provider (e.g., "Ibuprofen 200 mg two tablets orally every 6 hours as needed for pain"). PRN medication orders are for medications to be taken as needed (e.g., "Morphine 2 mg IV every 4 hours PRN for severe pain). Standing medication orders are pre-authorized orders for certain medications or treatments that can be administered under specific conditions without direct contact with the provider at that moment (e.g., "Administer oxygen at 2 liters per minute if oxygen saturation falls below 90%").

Treatment orders include orders for therapies and procedures, dietary orders, activity orders, and monitoring orders. Therapies orders include orders for physical therapy, occupational therapy, speech therapy, or other therapeutic interventions (e.g., "Physical therapy for 30 minutes daily to improve mobility"). Procedures orders include orders for specific medical or surgical procedures (e.g., "Perform chest X-ray and CBC prior to surgery"). Dietary orders include instructions regarding the patient's diet, including restrictions, special diets, or supplemental nutrition (e.g., "Low sodium diet, 1500 mg/day"). Activity orders are orders related to the patient's level of physical activity (e.g., "Bed rest with bathroom privileges" or "Ambulate three times daily"). Monitoring orders are orders for monitoring vital signs, blood glucose, or other parameters (e.g., "Check blood glucose levels before meals and at bedtime").

In addition to patient and provider information, orders 138 may require additional information for completing the orders. For example, a medication order may require i) medication information, e.g., medication name, formulation, strength, quantity, ii) dosage instructions, e.g., dosage, frequency, route of administration, duration of therapy, and iii) additional information, e.g., refill information, monitoring requirements, patient education, amount, administration instructions, i.e., frequency and duration. A diagnostic order may require i) test details, e.g., test name, test code, test category, ii) specific instructions, e.g., specimen requirements, preparation instructions, timing, special handling, and iii) clinical information, e.g., diagnosis/indication, relevant medical history, current medications.

In one or more embodiments, feedback 140 may be provided for an order generated by the recommendation component 124 of the order engine 116. Feedback 140 may be received directly from the clinician in the form of a survey. Feedback 140 may include amendments or alterations by the clinician to a suggested order provided by the recommendation component. Material added to or removed from an order suggested by the recommendation component 124 based on patient data may be used to update the content of future order suggestions. Feedback 140 associated with a suggested order may be provided by a clinician or other independent reviewer at a later time.

In one or more embodiments, discussions 142 are conversations between a) a clinician and a patient, b) the clinician and another clinician, or c) a clinician and a chatbot. Discussions 142 may also include a clinician talking aloud to themselves. Discussions 142 may be picked up by a listening device, e.g., microphone, on the clinician device 106 or located within the clinical environment. Discussions 142 are monitored for content that may trigger order generation. Discussions 142 may be recorded and saved to a patient's EHR.

In one or more embodiments, communications 144 are messages, e.g., e-mails, direct messages, texts, etc. Communications 144 may be generated by a patient, a clinician, and/or internal or external entities, e.g., laboratories. Communications 144 may be saved to a patient's EHR.

In one or more embodiments, updates 146 include receipt of or modifications to laboratory results, imaging and radiology reports, pathology results, and medication records. Laboratory results including blood tests, e.g., complete blood count (CBC), electrolytes, liver function tests, lipid panels, etc.; urine tests, e.g., urinalysis, urine culture; microbiology results, e.g., cultures, sensitivities, and other results related to infectious agents; and genetic tests, e.g., results from genetic or genomic testing, including markers for specific conditions. Imaging and radiology reports include X-rays, e.g., images and interpretations; CT scans, e.g., detailed cross-sectional images; Magnetic resonance imaging results; ultrasound, e.g., sonographic images and interpretations; and nuclear medicine, e.g., PET scans, bone scans. Pathology results include biopsy reports, e.g., histological findings from tissue samples; cytology, e.g., results from examining cells, such as Pap smears; and molecular pathology, e.g., results from tests like PCR, FISH, or other molecular assays. Medication records include current medications, e.g., a list of the prescribed, over-the-counter, and herbal medications; medication history, e.g., previous prescriptions, including doses and duration of use; and allergies and adverse reactions, e.g., documented drug allergies and any adverse reactions to medications.

In one or more embodiments, updates 146 include receipt of or modifications to treatment plans and orders, procedural and surgical records, and clinical notes and documentation. Treatment plans and orders include care plans, e.g., detailed treatment plans developed by healthcare providers, and orders, e.g., prescriptions, lab test orders, imaging orders, referrals to specialists. Procedural and surgical records include procedure notes, e.g., documentation of minor procedures, such as catheter insertions or wound care, as well as surgical reports, e.g., detailed reports from surgeries, including the type of surgery, findings, and outcomes. Clinical notes and documentation include progress notes, e.g., daily or visit-specific notes written by healthcare providers; discharge summaries, e.g., a summary of the patient's hospital stay, including final diagnoses, treatment provided, and follow-up instructions; and consultation notes, e.g., notes from specialist consultations.

In one or more embodiments, updates 146 include receipt of or modifications to vital signs and monitoring data, patient-reported outcomes, mental health data, and social and behavioral data. Vital signs and monitoring data include continuous monitoring, e.g., data from devices like heart monitors, blood glucose monitors, and wearable devices, as well as periodic measurements, e.g., routine vital signs taken during clinic visits or hospital stays. Patient-reported outcomes include surveys and questionnaires, e.g., information provided directly by the patient regarding symptoms, quality of life, and treatment satisfaction; pain scores, e.g., self-reported pain levels; and functional status, e.g., assessments of mobility, daily living activities, and cognitive function. Mental health data includes psychiatric evaluations, e.g., assessments of mental health, including diagnoses like depression or anxiety; counseling notes, e.g., documentation from therapy or counseling sessions; and psychometric test results, e.g., results from standardized tests like the MMPI or Beck Depression Inventory. Social and behavioral data includes lifestyle factors, e.g., smoking status, alcohol use, diet, exercise habits; social determinants of health, e.g., information about the patient's living situation, employment status, and access to healthcare resources; and substance use history, e.g., documentation of any history of substance abuse.

In one or more embodiments, queries 148 are specific requests to retrieve or filter patients for a medical order. Queries 148 may be based at least on a portion of a medical order defined by a clinician. Queries 148 may be generated and executed in real time. Continuous refinement of queries 148 facilitates narrowing down results from the queries and/or acts as validation checks. Queries 148 may be constructed using structured query language or other query language.

In one or more embodiments, clinician device 106 is a digital device that includes an interface 150. Interface 150 refers to hardware and/or software configured to facilitate communications between a user and practice management service 102. Interface 150 renders user interface elements, e.g., interface element 152, and receives input via user interface elements. Examples of interfaces include a graphical user interface (GUI), a command line interface (CLI), a haptic interface, and a voice command interface. Examples of user interface elements include checkboxes, radio buttons, dropdown lists, list boxes, buttons, toggles, text fields, date and time selectors, command lines, sliders, pages, and forms.

In an embodiment, different components of interface 150 are specified in different languages. The behavior of user interface elements is specified in a dynamic programming language such as JavaScript. The content of user interface elements is specified in a markup language, such as hypertext markup language (HTML) or XML User Interface Language (XUL). The layout of user interface elements is specified in a style sheet language such as Cascading Style Sheets (CSS). Alternatively, interface 150 is specified in one or more other languages, such as Java, C, or C++.

3. DETERMINING AN ORDER FOR A PATIENT USING MACHINE LEARNING

Figure 2:
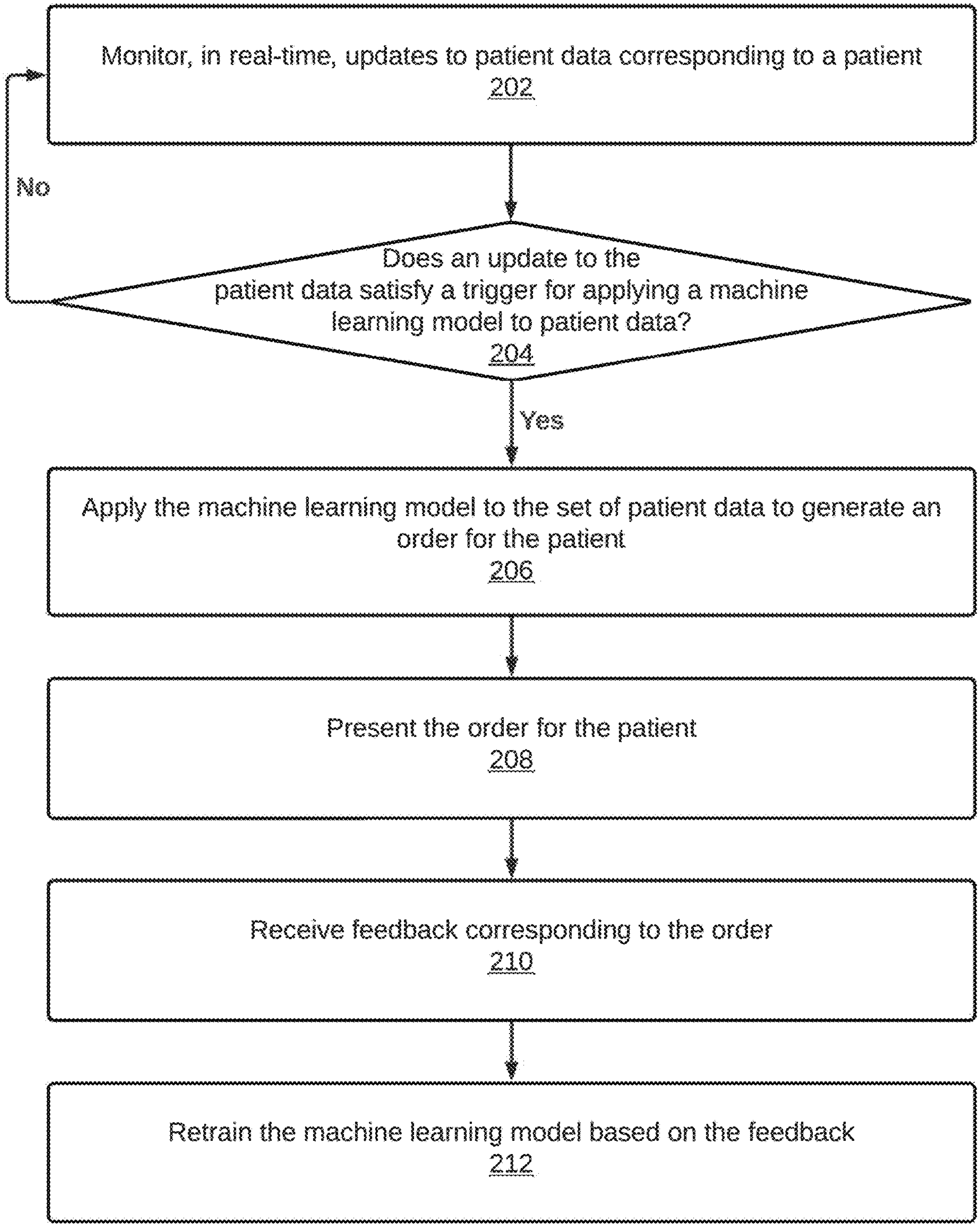
FIG. 2 illustrates an example set of operations for suggesting a medical order for a clinician to place for a patient in accordance with one or more embodiments.

FIG. 2 illustrates an example set of operations for suggesting an order for a clinician to place for a patient in accordance with one or more embodiments. One or more operations illustrated in FIG. 2 may be modified, rearranged, or omitted. Accordingly, the particular sequence of operations illustrated in FIG. 2 should not be construed as limiting the scope of one or more embodiments.

One or more embodiments monitor, in real-time, updates to patient data corresponding to a patient (Operation 202). Patient data may be received and processed by a data processing engine of a practice management service. Patient data may be updated by a clinician or other medical personnel. Updating patient data may occur prior to, during, or after a visit with the medical personnel. Updates to patient data may be received from outside sources, including laboratories, treatment facilities, and other clinical practices. Updates to patient data may be viewed by a clinician on a GUI.

One or more embodiments detect if the update to the patient data satisfies a trigger for applying a machine learning model to the set of patient data (Operation 204). When patient data is updated, i.e., laboratory results for a patient are received and/or added to an EHR of a patient, the system evaluates if the update satisfies predefined conditions or rules for triggering generating an order for a patient. Some updates to patient data may not necessarily trigger an order. Particular updates, e.g., laboratory results, may trigger generation of an order for patient follow-up in addition to an order for prescriptions.

One or more embodiments apply a machine learning model to the set of patient data to generate an order for the patient (Operation 206). Patient data, including the data that triggered the update, may be applied to a trained machine learning model. The machine learning model is trained to suggest an order based, at least in part, on the patient data. The machine learning model is trained with training data comprising sets of patient data and orders, e.g., for prescription or treatment, that correspond to patient data.

One or more embodiments present the order for the patient (Operation 208). The machine learning model(s) may determine that the patient data corresponds to one or more orders for the patient. The system presents the one or more orders to the clinician. The orders may be presented to the clinician in a GUI. The GUI may include an interface element for selection by the clinician to execute the orders. The GUI may include one or more interface elements for modifying the order. For example, the dosage or frequency of a medication may be modified by the clinician using a text editing function. The system may offer alternative medications, e.g., brand drugs or drugs, covered by the patient's insurance.

One or more embodiments receive feedback corresponding to the order (Operation 210). Feedback corresponding to the order may be received from the clinician. Feedback may include any modifications to the order suggested by the system that are made by the clinician prior to executing the order. Additionally, feedback may be provided by an independent reviewer of the patient data and the suggested order(s).

One or more embodiments retrain the machine learning model based on the feedback received (Operations 212). Using the feedback associated with the suggested order, the machine learning model may be retrained to provide more accurate suggestions for future orders.

4. DETERMINING A PATIENT FOR AN ORDER

Figure 3:
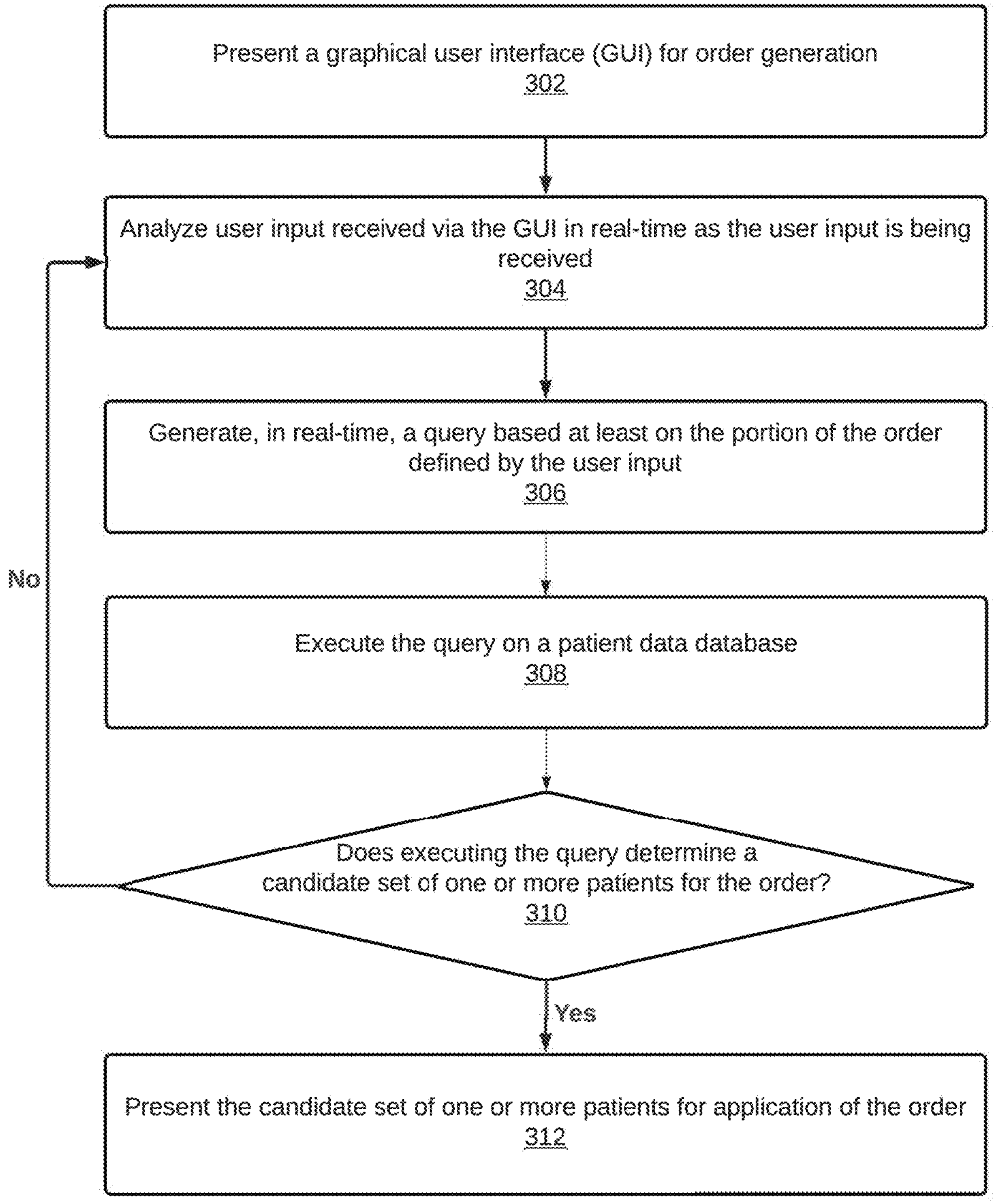
FIG. 3 illustrates an example set of operations for suggesting a patient based on content of a medical order in accordance with one or more embodiments.

FIG. 3 illustrates an example set of operations for suggesting a patient based on content of an order in accordance with one or more embodiments. One or more operations illustrated in FIG. 3 may be modified, rearranged, or omitted. Accordingly, the particular sequence of operations illustrated in FIG. 3 should not be construed as limiting the scope of one or more embodiments.

One or more embodiments present a graphical user interface (GUI) for order generation (Operation 302). A system for placing orders for patients may include a GUI for receiving order information. The GUI may include one or more text boxes for natural language entry of content of an order. A GUI may include dropdown menus for selecting types of orders. The GUI for medical order selection may include auto-complete search fields; fields to enter dosage, route, frequency of administration, duration, and special instructions; and checkboxes for indicating various features. A GUI for lab test order selection may include a search bar to select a lab test, e.g., CBC, BMP; options for selecting priority and frequency, e.g., Stat, once; and dropdown menus to select sample type, e.g., blood, urine.

One or more embodiments analyze user input received via the GUI in real time as the user input is being received (Operation 304). User input may include selection of items in a dropdown menu, selection of one or more checkboxes, and/or identification of one or more medications. User input may include natural language entry into a text box. Real-time monitoring captures keystrokes, selection, or input field change. User input may be validated in real time. To avoid errors, suggestions for dosage, frequency, and other attributes for medications and treatments may be suggested in dropdown menus and auto-complete search fields. Options for fields that are not applicable for a particular order may be phantomed or otherwise removed from being presented for selection to prevent accidental selection.

One or more embodiments generate, in real time, a query based at least on the portion of the order defined by the user input (Operation 306). As the clinician types an entry or makes a selection, e.g., medication name, dosage, route, etc., the data is captured in real time. The patient data is used to construct a query. As more information is received, the system refines the query. Refining the query assists in narrowing the results. Refining the query also provides validation checks for the results.

One or more embodiments execute the query on a patient data database (Operation 308). The query may be executed on a patient data database in real-time. As the query is updated as more information is received, the query may be executed/re-executed following updates. In executing the query, the system searches the database to determine patients with patient data that correspond to the query.

One or more embodiments determine if executing the query identifies a candidate set of one or more patients for application of the order (Operation 310). Executing the query against a patient data database may identify a candidate set of patients. Identifying candidate patients includes identifying patients that include patient data corresponding to the query. Identifying candidate patients may include identifying patients who have visited a medical professional within a particular time window from the current time, e.g., two weeks. Identifying a candidate set of patients may include identifying patients with patient data that has been updated within a particular time window from the current time, e.g., five days. As the query is updated, the candidate set of patients may be filtered and/or sorted.

One or more embodiments present the candidate set of one or more patients for application of the order (Operation 312). The candidate set of patients may be presented to the clinician in the GUI. The candidate set of patients may be presented in a dropdown menu. A menu of patient names may be incorporated into the "patient name" field for completing the order. The candidate set of patients may be sorted and presented in an order of relevance, with most likely candidate patients featured before less likely candidate patients. Selection of a candidate patient provides indication to the system that order should be applied to the selected candidate patient. Selection of a candidate patient may provide feedback to the system with regards to accuracy of the results. The feedback may be used to generate training data to retrain the one or more machine learning models used in query generation and execution.

5. DETERMINING MISSING DATA FOR ORDER COMPLETION

Figure 4:
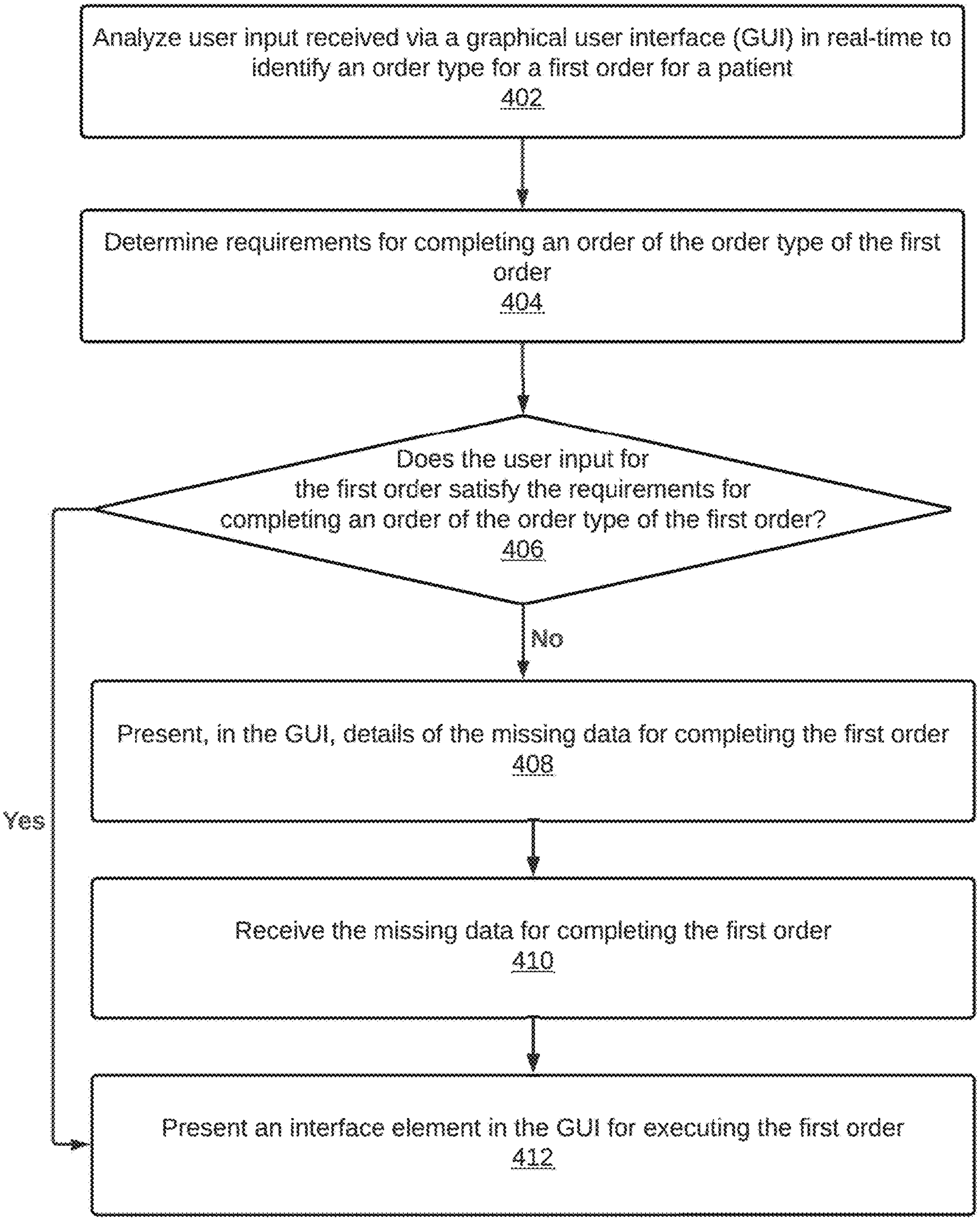
FIG. 4 illustrates an example set of operations for identifying missing elements in a medical order and prompting a clinician to enter the missing elements in accordance with one or more embodiments.

FIG. 4 illustrates an example set of operations for identifying missing elements in a medical order and prompting a clinician to enter the missing elements in accordance with one or more embodiments. One or more operations illustrated in FIG. 4 may be modified, rearranged, or omitted. Accordingly, the particular sequence of operations illustrated in FIG. 4 should not be construed as limiting the scope of one or more embodiments.

One or more embodiments analyze user input received via a graphical user interface (GUI) in real time to identify an order type for a first order for a patient (Operation 402). As noted above, a system for placing orders for patients may include a GUI for receiving order information. The GUI may include one or more text boxes for natural language entry of an order. The GUI may include dropdown menus for selecting types of orders. A GUI for medical order selection may include auto-complete search fields, fields to enter dosage, route, frequency of administration, duration, and special instructions, and checkboxes for indicating various features. A GUI for lab test order selection may include a search bar to select a lab test, e.g., CBC, BMP, options for selecting priority and frequency, e.g., Stat, once, and dropdown menus to select sample type, e.g., blood, urine.

One or more embodiments determine requirements for completing an order of the order type of the first order (Operation 404). The system analyzes the information associated with the user input as the clinician enters the information to determine the type of order, e.g., medication prescription, treatment, lab request, and the requirements for completing the order. The system may use machine learning models trained to determine a type of an order based on information associated with the order. Training sets for training the machine learning model may include sets of features or requirements for completing an order and the associated order.

One or more embodiments determine if the user input for the first order satisfies the requirements for completing an order of the order type of the first order (Operation 406). After identifying the type of order and the requirements for completing the order, the system compares the information input by the clinician to determine if the order is complete, i.e., includes the required information for executing the order.

One or more embodiments present, in the GUI, details of the missing data for completing the first order (Operation 408). When the system determines that the information input by the clinician is incomplete, i.e., missing elements, the system may display, in the GUI, suggestions for the one or more missing elements. The system may present interface elements with options for selection by the clinician for the one or more missing elements.

One or more embodiments receive the missing data for completing the first order (Operation 410). The one or more missing elements may be added to the order as the selections and/or entries are made. When the system provides interface elements with suggestions for the missing elements, selection of the interface element provides the missing element for completing the order.

One or more embodiments present an interface element in the GUI for executing the first order (Operation 412). Upon receipt of the missing data and completion of the order, the system provides an interface element for selection by the clinician for executing the order.

6. DASHBOARD FOR A PATIENT MANAGEMENT SYSTEM

A detailed example is described below for purposes of clarity. Components and/or operations described below should be understood as one specific example that may not be applicable to certain embodiments. Accordingly, components and/or operations described below should not be construed as limiting the scope of any of the claims.

Figure 5:
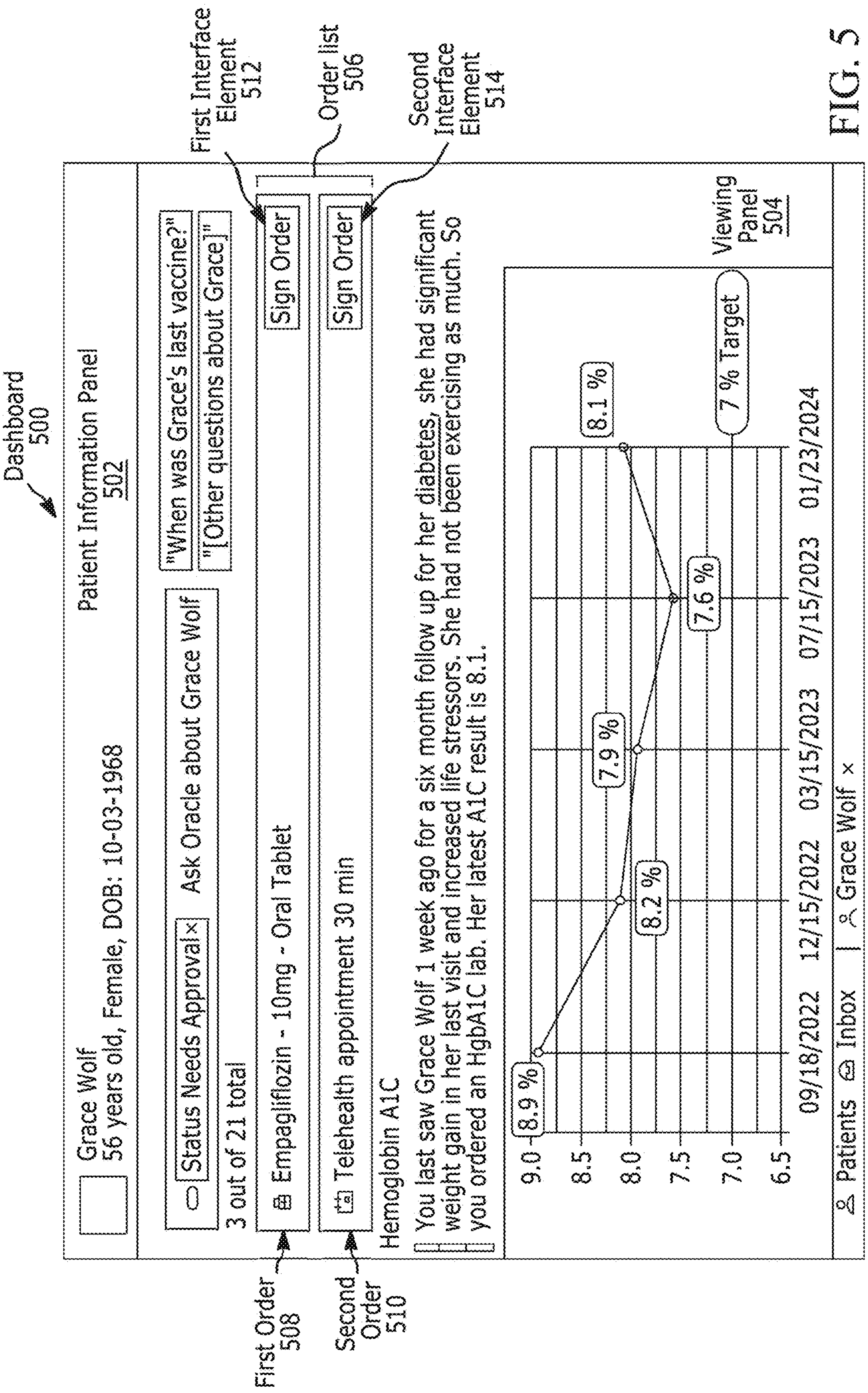
FIG. 5 illustrates an example dashboard of a patient management system.

FIG. 5 illustrates a dashboard 500 for patient management. As shown, dashboard 500 includes a patient information panel 502, a viewing panel 504, and an order list 506. Patient information panel 502 displays detailed patient information, e.g., patient name, age, sex, and date of birth of the patient. The viewing panel 504 displays results and other medical information associated with the patient. The order list 506 is a list of orders or items generated by the system in response to the results displayed in the viewing panel 504. The order list 506 includes a first order 508 and a second order 510. The first order 508 may be executed by a clinician by selecting a first interface element 512. The second order 510 may be executed by a clinician selecting a second interface element 514.

As detailed in the patient information panel 502, the dashboard 500 displays a patient record for a patient named Grace Wolf. She is a 56-year-old woman born on Oct. 3, 1968. As detailed in the viewing panel 504, lab results for Ms. Wolf indicate an increase in Hemoglobin A1C. Based on the lab results for Ms. Wolf, the first order 508 suggested by the system based on the test results viewable in the viewing panel 504 is a prescription for Empagliflozin 10 mg Oral Tablet. The second order 510 suggested by the system based on the test results viewable in the viewing panel 504 is a request for a 30-minute telehealth appointment with Ms. Wolf. The prescription may be executed by a clinician by selecting the first interface element 512 that reads "Sign Order". The request may be executed by the clinician by selecting the second interface element 514 that reads "Sign Order".

7. CHAT CONVERSATION IN A PATIENT MANAGEMENT SYSTEM

A detailed example is described below for purposes of clarity. Components and/or operations described below should be understood as one specific example that may not be applicable to certain embodiments. Accordingly, components and/or operations described below should not be construed as limiting the scope of any of the claims.

Figure 6A:
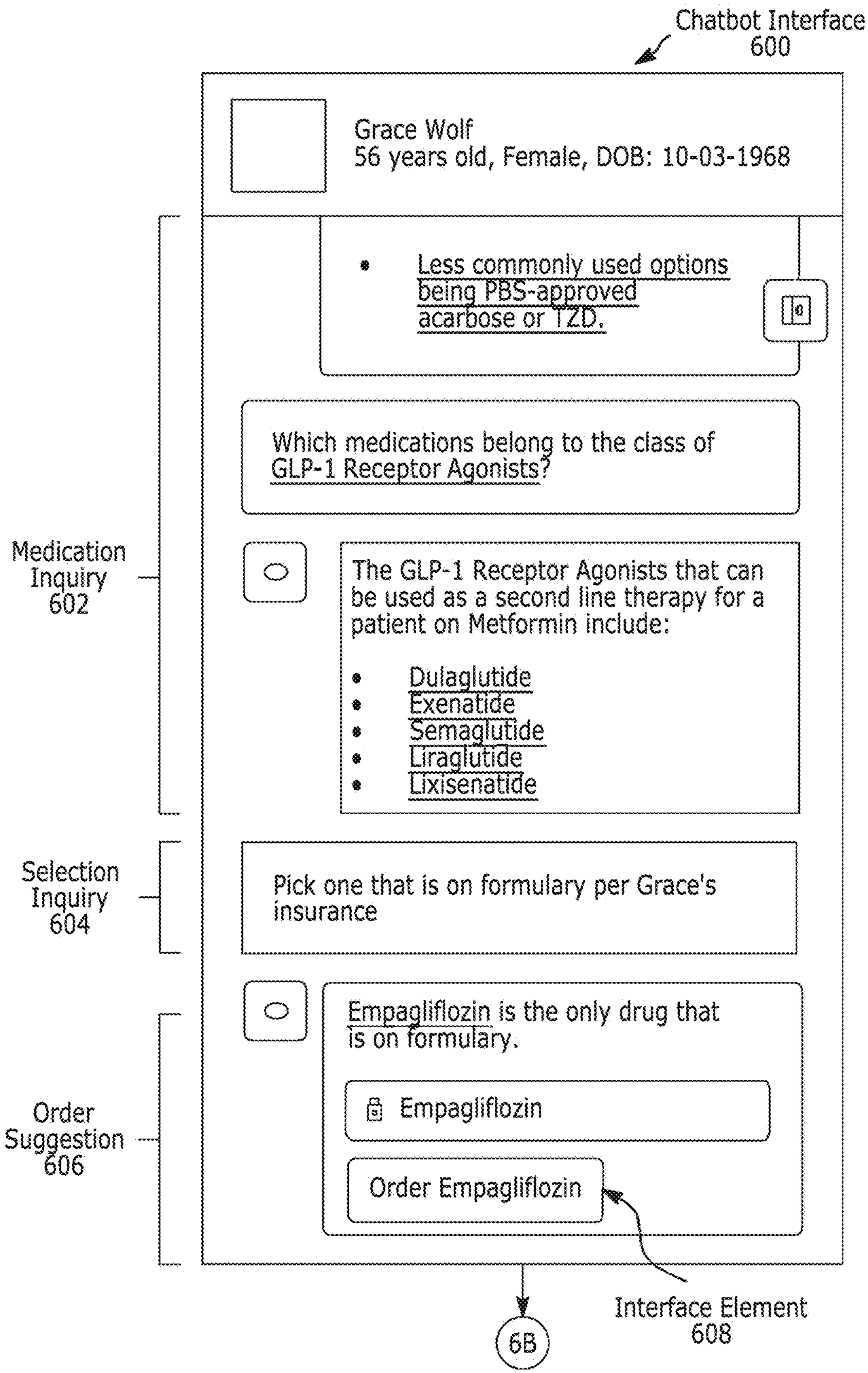
FIGS. 6A and 6B illustrate an example chat conversation in a patient management system.
Figure 6B:
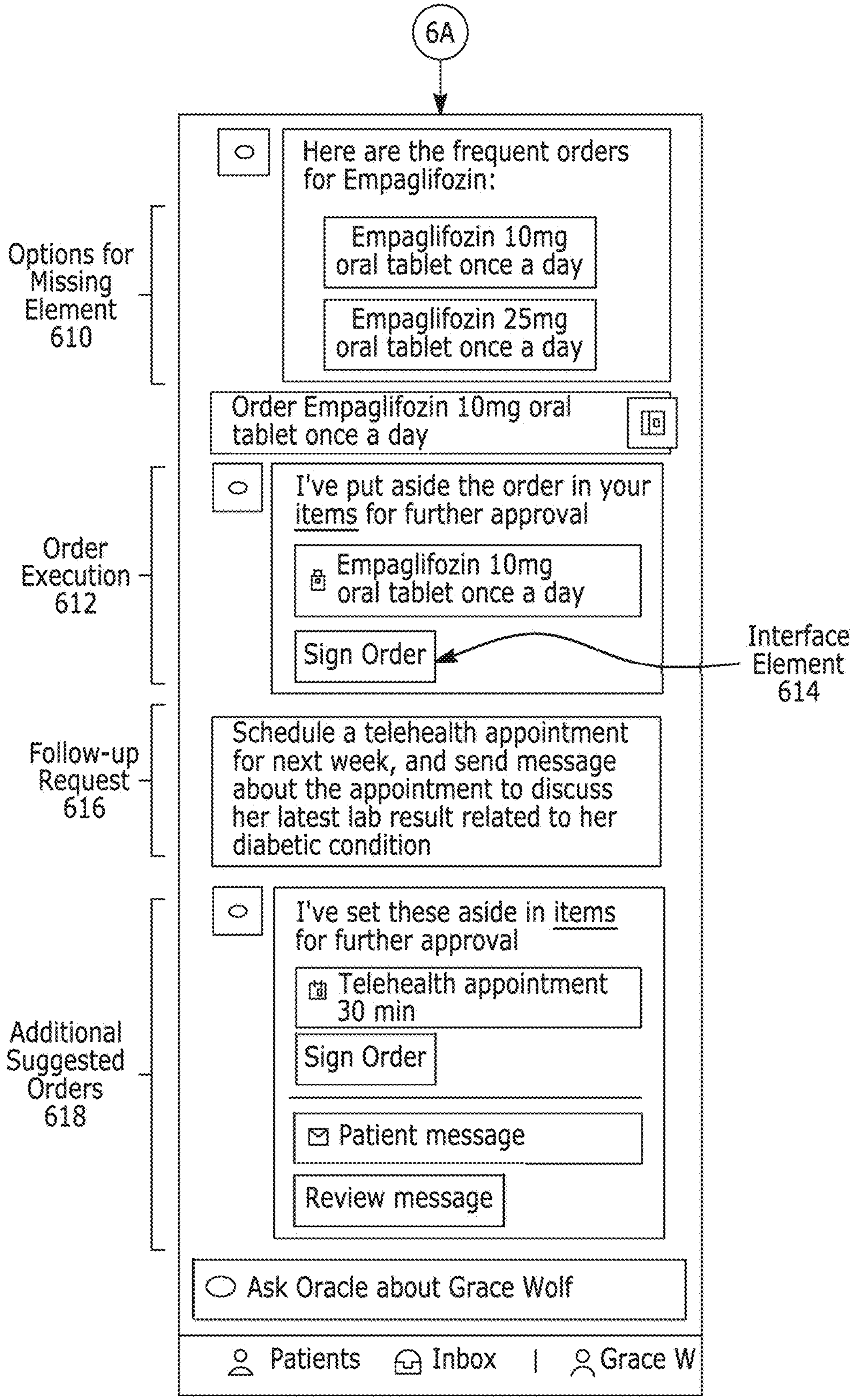

FIGS. 6A and 6B illustrate a chat conversation between a clinician and an AI chatbot with regards to a patient, Grace Wolf. The chat conversation begins with a medication inquiry 602, followed by a selection inquiry 604, then an order suggestion 606. The chat conversation continues with options for missing element 610, order execution 612, follow-up request 616, and additional suggested orders 618.

Medication inquiry 602 includes an inquiry by the clinician regarding a medication. The AI chatbot receives the inquiry and provides a list of medications that correspond to the inquiry. Selection inquiry 604 includes the clinician requesting from the AI chatbot identification of a medication that is accepted by Ms. Wolf's insurance. The inquiry by the clinician triggers the system to generate a suggested order for Ms. Wolf. Order suggestion 606 includes an interface element 608. Selection of interface element 608 causes the system to validate the order, ensuring that the order is complete and not missing information.

Following selection of interface element 608 by the clinician, the system determines that the order is incomplete, i.e., is missing elements. The system identifies the elements missing from the order and presents the clinician with options for missing element 610. Selection of one of the options for missing element 610 results in the system confirming that the order contains the required information. Once the order is confirmed, the system order is ready to be executed. Order execution 612 includes an interface element 614 for selection by the clinician for signing the order.

After signing the order, the clinician provides the AI chatbot with a follow-up request 616. In response to the follow-up request, the system generates additional suggested orders 616.

8. PRACTICAL APPLICATIONS, ADVANTAGES & IMPROVEMENTS

A patient ordering system that utilizes machine learning models offers significant advantages, including improved accuracy and safety, efficiency gains, personalized patient care, and cost reduction. The use of machine learning models may significantly reduce human errors in order entry, particularly related to drug interactions, dosage errors, or inappropriate orders. By continuously learning from past data, the system can better anticipate and mitigate risks, leading to safer patient care. Automated recommendations and order processing reduce the time clinicians spend on routine tasks, allowing them to focus more on patient care.

By optimizing the order entry process, redundancies and unnecessary steps are reduced. The use of machine learning models allows for highly personalized treatment plans that are tailored to individual patient needs, improving treatment efficacy. With ML-driven insights, healthcare providers can make more informed decisions, leading to improved patient outcomes.

Efficient ordering and resource allocation reduce waste and unnecessary expenditures. By predicting and preventing complications, the system can reduce the need for costly interventions or hospital readmissions.

A patient ordering system that utilizes machine learning models offers significant advantages in improving healthcare delivery, including, for example, personalized treatment plans and enhanced decision support and efficiency. By continuously learning from data, such a system can adapt and improve over time, leading to better patient outcomes, reduced costs, and optimized resource use.

9. HARDWARE OVERVIEW

According to one embodiment, the techniques described herein are implemented by one or more special-purpose computing devices. The special-purpose computing devices may be hard-wired to perform the techniques, or may include digital electronic devices such as one or more application-specific integrated circuits (ASICs), field programmable gate arrays (FPGAs), or network processing units (NPUs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, FPGAs, or NPUs with custom programming to accomplish the techniques. The special-purpose computing devices may be desktop computer systems, portable computer systems, handheld devices, networking devices or any other device that incorporates hard-wired and/or program logic to implement the techniques.

Figure 7:
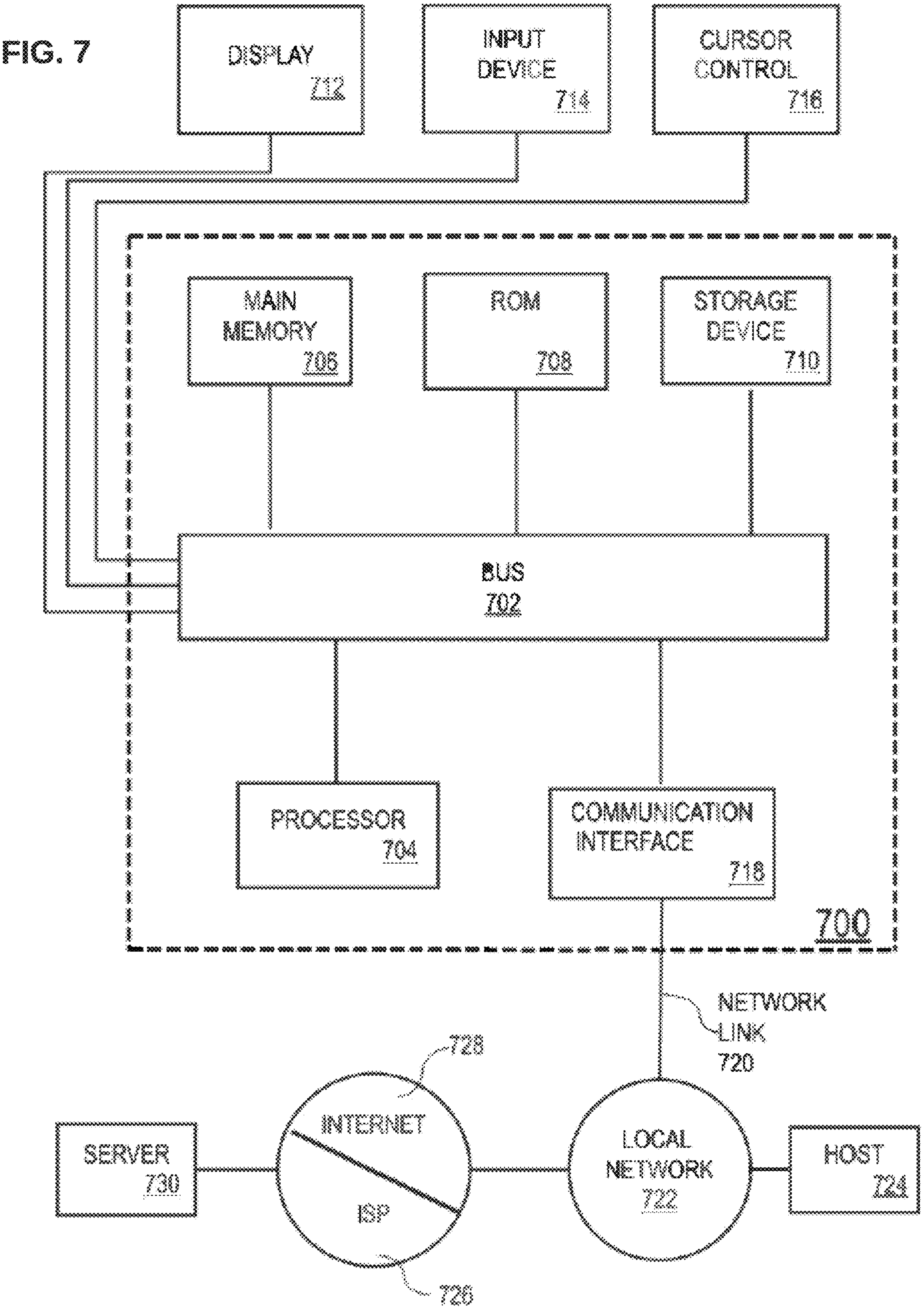
FIG. 7 shows a block diagram that illustrates a computer system in accordance with one or more embodiments.

For example, FIG. 7 is a block diagram that illustrates a computer system 700 upon which an embodiment of the disclosure may be implemented. Computer system 700 includes a bus 702 or other communication mechanism for communicating information, and a hardware processor 704 coupled with bus 702 for processing information. Hardware processor 704 may be, for example, a general purpose microprocessor.

Computer system 700 also includes a main memory 706, such as a random access memory (RAM) or other dynamic storage device, coupled to bus 702 for storing information and instructions to be executed by processor 704. Main memory 706 also may be used for storing temporary variables or other intermediate information during execution of instructions to be executed by processor 704. Such instructions, when stored in non-transitory storage media accessible to processor 704, render computer system 700 into a special-purpose machine that is customized to perform the operations specified in the instructions.

Computer system 700 further includes a read only memory (ROM) 708 or other static storage device coupled to bus 702 for storing static information and instructions for processor 704. A storage device 710, such as a magnetic disk, optical disk, or a Solid State Drive (SSD) is provided and coupled to bus 702 for storing information and instructions.

Computer system 700 may be coupled via bus 702 to a display 712, such as a cathode ray tube (CRT), for displaying information to a computer user. An input device 714, including alphanumeric and other keys, is coupled to bus 702 for communicating information and command selections to processor 704. Another type of user input device is cursor control 716, such as a mouse, a trackball, or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane.

Computer system 700 may implement the techniques described herein using customized hard-wired logic, one or more ASICs or FPGAs, firmware and/or program logic which in combination with the computer system causes or programs computer system 700 to be a special-purpose machine. According to one embodiment, the techniques herein are performed by computer system 700 in response to processor 704 executing one or more sequences of one or more instructions contained in main memory 706. Such instructions may be read into main memory 706 from another storage medium, such as storage device 710. Execution of the sequences of instructions contained in main memory 706 causes processor 704 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 710. Volatile media includes dynamic memory, such as main memory 706. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, content-addressable memory (CAM), and ternary content-addressable memory (TCAM).

Storage media is distinct from but may be used in conjunction with transmission media. Transmission media participates in transferring information between storage media. For example, transmission media includes coaxial cables, copper wire and fiber optics, including the wires that comprise bus 702. Transmission media can also take the form of acoustic or light waves, such as those generated during radio-wave and infra-red data communications.

Various forms of media may be involved in carrying one or more sequences of one or more instructions to processor 704 for execution. For example, the instructions may initially be carried on a magnetic disk or solid state drive of a remote computer. The remote computer can load the instructions into its dynamic memory and send the instructions over a telephone line using a modem. A modem local to computer system 700 can receive the data on the telephone line and use an infra-red transmitter to convert the data to an infra-red signal. An infra-red detector can receive the data carried in the infra-red signal and appropriate circuitry can place the data on bus 702. Bus 702 carries the data to main memory 706, from which processor 704 retrieves and executes the instructions. The instructions received by main memory 706 may optionally be stored on storage device 710 either before or after execution by processor 704.

Computer system 700 also includes a communication interface 718 coupled to bus 702. Communication interface 718 provides a two-way data communication coupling to a network link 720 that is connected to a local network 722. For example, communication interface 718 may be an integrated services digital network (ISDN) card, cable modem, satellite modem, or a modem to provide a data communication connection to a corresponding type of telephone line. As another example, communication interface 718 may be a local area network (LAN) card to provide a data communication connection to a compatible LAN. Wireless links may also be implemented. In any such implementation, communication interface 718 sends and receives electrical, electromagnetic or optical signals that carry digital data streams representing various types of information.

Network link 720 typically provides data communication through one or more networks to other data devices. For example, network link 720 may provide a connection through local network 722 to a host computer 724 or to data equipment operated by an Internet Service Provider (ISP) 726. ISP 726 in turn provides data communication services through the world wide packet data communication network now commonly referred to as the "Internet" 728. Local network 722 and Internet 728 both use electrical, electromagnetic or optical signals that carry digital data streams. The signals through the various networks and the signals on network link 720 and through communication interface 718, which carry the digital data to and from computer system 700, are example forms of transmission media.

Computer system 700 can send messages and receive data, including program code, through the network(s), network link 720 and communication interface 718. In the Internet example, a server 730 might transmit a requested code for an application program through Internet 728, ISP 726, local network 722 and communication interface 718.

The received code may be executed by processor 704 as it is received, and/or stored in storage device 710, or other non-volatile storage for later execution.

8. MISCELLANEOUS; EXTENSIONS

Unless otherwise defined, all terms (including technical and scientific terms) are to be given their ordinary and customary meaning to a person of ordinary skill in the art, and are not to be limited to a special or customized meaning unless expressly so defined herein.

This application may include references to certain trademarks. Although the use of trademarks is permissible in patent applications, the proprietary nature of the marks should be respected and every effort made to prevent their use in any manner which might adversely affect their validity as trademarks.

Embodiments are directed to a system with one or more devices that include a hardware processor and that are configured to perform any of the operations described herein and/or recited in any of the claims below.

In an embodiment, one or more non-transitory computer readable storage media comprises instructions which, when executed by one or more hardware processors, cause performance of any of the operations described herein and/or recited in any of the claims.

In an embodiment, a method comprises operations described herein and/or recited in any of the claims, the method being executed by at least one device including a hardware processor.

Any combination of the features and functionalities described herein may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. One or more non-transitory computer readable media comprising instructions which, when executed by one or more hardware processors, cause performance of operations comprising:

obtaining training data sets, wherein a training data set, of the training data sets, comprises:

a first set of patient data corresponding to a first patient; and a first order for a prescription or treatment that has been placed for the first patient;

training a first machine learning model to generate orders based on patient data sets;

monitoring, in real-time, content of a first set of updates to a second set of patient data corresponding to a second patient;

based on the real-time monitoring of the content of the first set of updates to the second set of patient data, determining that the content of the first set of updates does not satisfy a trigger for applying the first machine learning model to the second set of patient data to generate an order for the second patient, the trigger comprising one or more predefined conditions;

in response to determining that the content of the first set of updates does not satisfy the trigger, refraining from applying the first machine learning model to the second set of patient data;

monitoring, in real-time, content of a second set of updates to the second set of patient data corresponding to the second patient;

based on the real-time monitoring of the content of the second set of updates to the second set of patient data, determining that the content of the second set of updates satisfies the trigger for applying the first machine learning model to the second set of patient data to generate an order for the second patient;

in response to determining that the content of the second set of updates satisfies the trigger, applying the first machine learning model to the second set of patient data to generate the order for the second patient;

presenting, in a user interface, the order generated by the first machine learning model for the second patient;

receiving, via the user interface, feedback corresponding to the order generated by the first machine learning model, wherein the feedback comprises one or more modifications to the order received in response to presenting the order; and based on the feedback corresponding to the one or more modifications of the order generated by the first machine learning model, retraining the first machine learning model using the one or more modifications to the order as training data associated with the second set of patient data.

2. The one or more non-transitory computer readable media of claim 1, wherein determining that the content of the second set of updates satisfies the trigger for applying the first machine learning model comprises:

applying a second machine learning model to the second set of patient data to determine that one or more orders need to be generated for the second patient.

3. The one or more non-transitory computer readable media of claim 1, wherein monitoring the second set of updates to the second set of patient data comprises:

analyzing, in real-time, a discussion between the second patient and a medical professional, wherein determining that the content of the second set of updates satisfies the trigger is based on content identified from the discussion.

4. The one or more non-transitory computer readable media of claim 3, wherein analyzing the discussion comprises:

analyzing a chat conversation between the second patient and the medical professional.

5. The one or more non-transitory computer readable media of claim 1, wherein monitoring the second set of updates to the second set of patient data comprises analyzing, in real-time, communication between medical professionals that is associated with the second patient, wherein determining that the content of the second set of updates satisfies the trigger is based on the communication between the medical professionals.

6. The one or more non-transitory computer readable media of claim 1, wherein monitoring the second set of updates to the second set of patient data comprises:

detecting at least a portion of the second set of patient data that is being displayed on a graphical user interface (GUI), wherein determining that the content of the second set of updates satisfies the trigger is based on the portion of the second set of patient data.

7. The one or more non-transitory computer readable media of claim 1, wherein presenting the order comprises:

an AI-based chatbot presenting the order to a medical professional within a chatbot interface.

8. The one or more non-transitory computer readable media of claim 1, wherein the content of the first set of updates comprises at least one of a laboratory result, a vital sign, a diagnostic imaging result, an updated symptom report, or data received from a wearable device or remote monitoring system associated with the second patient, wherein the content of the second set of updates comprises at least one of a laboratory result, a vital sign, a diagnostic imaging result, an updated symptom report, or data received from a wearable device or remote monitoring system associated with the second patient.

9. The one or more non-transitory computer readable media of claim 1, wherein determining that the content of the first set of updates does not satisfy the trigger comprises:

comparing at least a portion of the content of the first set of updates to a predefined threshold; and determining that the at least a portion of the content of the first set of updates is within the predefined threshold, wherein determining that the content of the second set of updates satisfies the trigger comprises:

comparing at least a portion of the content of the second set of updates to the predefined threshold; and determining that the at least a portion of the content of the second set of updates is outside the predefined threshold.

10. The one or more non-transitory computer readable media of claim 1, wherein the trigger comprises at least one of (i) a codified set of rules, or (ii) a set of automatically-learned patterns, the codified set of rules and the set of automatically-learned patterns each capturing one or more conditions for prompting creation or modification of medical orders, wherein determining whether content of a particular set of updates satisfies the trigger comprises evaluating the content of the particular set of updates against the codified set of rules and the set of automatically-learned patterns.

11. A method comprising:

obtaining training data sets, wherein a training data set, of the training data sets, comprises:

a first set of patient data corresponding to a first patient; and a first order for a prescription or treatment that has been placed for the first patient;

training a first machine learning model to generate orders based on patient data sets;

monitoring, in real-time, content of a first set of updates to a second set of patient data corresponding to a second patient;

based on the real-time monitoring of the content of the first set of updates to the second set of patient data, determining that the content of the first set of updates does not satisfy a trigger for applying the first machine learning model to the second set of patient data to generate an order for the second patient, the trigger comprising one or more predefined conditions;

in response to determining that the content of the first set of updates does not satisfy the trigger, refraining from applying the first machine learning model to the second set of patient data;

monitoring, in real-time, content of a second set of updates to the second set of patient data corresponding to the second patient;

based on the real-time monitoring of the content of the second set of updates to the second set of patient data, determining that the content of the second set of updates satisfies the trigger for applying the first machine learning model to the second set of patient data to generate an order for the second patient;

in response to determining that the content of the second set of updates satisfies the trigger, applying the first machine learning model to the second set of patient data to generate the order for the second patient;

presenting, in a user interface, the order generated by the first machine learning model for the second patient;

receiving, via the user interface, feedback corresponding to the order generated by the first machine learning model, wherein the feedback comprises one or more modifications to the order received in response to presenting the order; and based on the feedback corresponding to the one or more modifications of the order generated by the first machine learning model, retraining the first machine learning model using the one or more modifications to the order as training data associated with the second set of patient data, wherein the method is performed by at least one device including a hardware processor.

12. The method of claim 11, wherein determining that the content of the second set of updates satisfies the trigger for applying the first machine learning model comprises:

applying a second machine learning model to the second set of patient data to determine that one or more orders need to be generated for the second patient.

13. The method of claim 11, wherein monitoring the second set of updates to the second set of patient data comprises:

analyzing, in real-time, a discussion between the second patient and a medical professional, wherein determining that the content of the second set of updates satisfies the trigger is based on content identified from the discussion.

14. The method of claim 13, wherein analyzing the discussion comprises:

analyzing a chat conversation between the second patient and the medical professional.

15. The method of claim 11, wherein monitoring the second set of updates to the second set of patient data comprises analyzing, in real-time, communication between medical professionals that is associated with the second patient, wherein determining that the content of the second set of updates satisfies the trigger is based on the communication between the medical professionals.

16. The method of claim 11, wherein monitoring the second set of updates to the second set of patient data comprises:

detecting at least a portion of the second set of patient data that is being displayed on a graphical user interface (GUI), wherein determining that the content of the second set of updates satisfies the trigger is based on the portion of the second set of patient data.

17. The method of claim 8, wherein presenting the order comprises:

an AI-based chatbot presenting the order to a medical professional within a chatbot interface.

18. A system comprising:

at least one device including a hardware processor;

the system being configured to perform operations comprising:

obtaining training data sets, wherein a training data set, of the training data sets, comprises:

a first set of patient data corresponding to a first patient; and a first order for a prescription or treatment that has been placed for the first patient;

training a first machine learning model to generate orders based on patient data sets;

monitoring, in real-time, content of a first set of updates to a second set of patient data corresponding to a second patient;

based on the real-time monitoring of the content of the first set of updates to the second set of patient data, determining that the content of the first set of updates does not satisfy a trigger for applying the first machine learning model to the second set of patient data to generate an order for the second patient, the trigger comprising one or more predefined conditions;

in response to determining that the content of the first set of updates does not satisfy the trigger, refraining from applying the first machine learning model to the second set of patient data;

monitoring, in real-time, content of a second set of updates to the second set of patient data corresponding to the second patient;

based on the real-time monitoring of the content of the second set of updates to the second set of patient data, determining that the content of the second set of updates satisfies the trigger for applying the first machine learning model to the second set of patient data to generate an order for the second patient;

in response to determining that the content of the second set of updates satisfies the trigger, applying the first machine learning model to the second set of patient data to generate the order for the second patient;

presenting, in a user interface, the order generated by the first machine learning model for the second patient;

receiving, via the user interface, feedback corresponding to the order generated by the first machine learning model, wherein the feedback comprises one or more modifications to the order received in response to presenting the order; and based on the feedback corresponding to the one or more modifications of the order generated by the first machine learning model, retraining the first machine learning model using the one or more modifications to the order as training data associated with the second set of patient data.

19. The system of claim 18, wherein determining that the content of the second set of updates satisfies the trigger for applying the first machine learning model comprises:

applying a second machine learning model to the second set of patient data to determine that one or more orders need to be generated for the second patient.

20. The system of claim 18, wherein monitoring the second set of updates to the second set of patient data comprises:

analyzing, in real-time, a discussion between the second patient and a medical professional, wherein determining that the content of the second set of updates satisfies the trigger is based on content identified from the discussion.

21. The system of claim 20, wherein analyzing the discussion comprises:

analyzing a chat conversation between the second patient and the medical professional.

22. The system of claim 18, wherein monitoring the second set of updates to the second set of patient data comprises analyzing, in real-time, communication between medical professionals that is associated with the second patient, wherein determining that the content of the second set of updates satisfies the trigger is based on the communication between the medical professionals.

23. The system of claim 18, wherein monitoring the second set of updates to the second set of patient data comprises:

detecting at least a portion of the second set of patient data that is being displayed on a graphical user interface (GUI), wherein determining that the content of the second set of updates satisfies the trigger is based on the portion of the second set of patient data.

* * * * *